(12) United States Patent
Cammann et al.

(10) Patent No.: US 6,296,685 B1
(45) Date of Patent: Oct. 2, 2001

(54) DEVICE AND METHOD FOR SAMPLING IN LIQUID PHASES USING A DIFFUSION BODY AND AN ANALYTE-BINDING PHASE

(75) Inventors: Karl Cammann, Akazienallee 1, D-48155 Muenster (DE); Thomas Brendel, Meunster (DE)

(73) Assignee: Karl Cammann, Muenster (DE)

( * ) Notice: Subject to any disclaimer, the term of this patent is extended or adjusted under 35 U.S.C. 154(b) by 0 days.

(21) Appl. No.: 09/381,005

(22) PCT Filed: Mar. 9, 1998

(86) PCT No.: PCT/DE98/00705

§ 371 Date: Nov. 10, 1999

§ 102(e) Date: Nov. 10, 1999

(87) PCT Pub. No.: WO98/41838

PCT Pub. Date: Sep. 24, 1998

(30) Foreign Application Priority Data

Mar. 14, 1997 (DE) ............................................. 197 10 525

(51) Int. Cl.[7] ........................................................ B01D 53/22
(52) U.S. Cl. ..................... 95/45; 95/82; 95/90; 96/4; 96/101; 96/108
(58) Field of Search ..................... 95/45–56, 82–89; 96/4–14, 101–107

(56) References Cited

U.S. PATENT DOCUMENTS

| | | |
|---|---|---|
| 3,751,879 | 8/1973 | Allington . |
| 3,924,219 | 12/1975 | Braun . |
| 4,040,805 * | 8/1977 | Nelms et al. .................. 96/4 |
| 4,151,060 * | 4/1979 | Isenberg ........................ 96/4 X |
| 4,208,371 * | 6/1980 | Kring ............................ 96/10 X |
| 4,240,912 | 12/1980 | Stumpf et al. . |
| 4,269,804 * | 5/1981 | Kring ............................ 96/10 X |
| 4,433,982 * | 2/1984 | Odernheimer et al. ......... 96/4 |
| 4,541,268 * | 9/1985 | Odernheimer .................. 96/4 X |
| 4,856,147 * | 8/1989 | Kohlheb et al. ................ 96/10 X |
| 4,904,449 | 2/1990 | Heckmann . |
| 4,942,135 | 7/1990 | Zaromb . |
| 5,053,060 * | 10/1991 | Kopf-Sill et al. ............... 96/6 X |
| 5,910,450 | 6/1999 | Manns et al. . |

FOREIGN PATENT DOCUMENTS

| | | |
|---|---|---|
| 37 35 307 A1 | 4/1989 | (DE) . |
| 195 38 075 C1 | 11/1996 | (DE) . |
| 195 33 510 A1 | 3/1997 | (DE) . |
| 0 282 901 A2 | 9/1988 | (EP) . |
| 0 714 020 A2 | 5/1996 | (EP) . |
| 2 211 295 A | 6/1989 | (GB) . |
| 60-56261 | 4/1985 | (JP) . |
| WO 95/05591 | 2/1995 | (WO) . |
| WO 96/07885 | 3/1996 | (WO) . |

OTHER PUBLICATIONS

Joensson J.A., et al.; "Supported Liquid Membrane Techniques For Sample Preparation and Enrichment in Environmental and Biological Analysis"; Trends in Analytical Chemistry, vol. 11, No. 3; Mar. 1, 1992; pp. 106–114; Elsevier Science Publishers B.V. (see p. 106, right–hand Col.—p. 108, left–hand Col.; Figures 1–3).

JP 60–56261; Patent Abstracts of Japan; P–377 Aug. 2, 1985, vol. 9, No. 18; Serum Sampler for Examination; Takeshi Sonoda.

* cited by examiner

Primary Examiner—Robert H. Spitzer
(74) Attorney, Agent, or Firm—Marshall & Melhorn, LLC

(57) ABSTRACT

A diffusion collector for analytes contained in liquid phases includes a planar housing which has channel-like cavities. A collecting phase is inserted into these channel-like cavities. The collecting phase is covered by a diffusion membrane through which the analyte can pass. The housing has at least one incoming pipe and one outgoing pipe allowing the fluid medium to pass through the channel-like cavities perpendicular to the direction of diffusion.

24 Claims, 1 Drawing Sheet

DEVICE AND METHOD FOR SAMPLING IN LIQUID PHASES USING A DIFFUSION BODY AND AN ANALYTE-BINDING PHASE

BACKGROUND OF THE INVENTION

1. Field of the Invention

The present invention concerns a diffusion collector for the so-called passive sample-taking of gaseous analytes or analytes dissolved in a liquid (dispensing phase) with a semipermeable, transport-controlling diffusion membrane, which prefers the analytes, and an analyte-selective ad- or absorption means for the purpose of increasing the analyte concentration (collecting or receiving phase).

The main area of application of the device according to the invention is the monitoring of environment-relevant substances, mainly in air and water samples (or the collection of volatile analytes in soil samples). The advantages of the passive sample-taking, such as simplicity (construction of badges) and no energy requirement whatsoever are sufficiently well known. For the purpose of monitoring the environment there is a large demand for simply constructed passive sample collectors, that are easy to use, which can collect the materials (analytes) of interest in a substantially shorter time, so as to be able to determine short-term peak values as well. For monitoring the work place, correspondingly suitable collecting badges are needed, which can be easily carried on the human body and which can perform satisfactorily without electrically driven pumps and nevertheless permit the taking of samples in comparable time intervals.

Commercially available diffusion sample-taking devices for collecting volatile materials are mainly based on the use of activated charcoal as an adsorption means of low specificity, which, for example, is strongly adversely affected by water vapor (moisture). The size of the diffusion surface is between 2 and 20 cm$^2$, and the diffusion path amounts to about 10 mm, These result in material-specific absorption rates of only 5 to 50 cm$^3$/min. Because the analytes can be almost completely desorbed again from the activated charcoal by a solvent elution process, during which process, however, a dilution by the solvent takes place, these collectors are almost exclusively suitable for high analyte concentrations and long sample-taking periods (several hours to a number of weeks).

The diffusion sample taking devices, which are based on organic polymers or the like, where in addition to the solvent desorption usually the more effective thermal desorption is also possible, are almost all based on glass tubes of the type known from the active sample-taking process involving the use of a pump. These collectors, however, have only a small diffusion cross-section(about 0.1 cm$^2$), and with a diffusion path of <<10 mm, very low absorption rates of less than 0.5 cm$^3$/min result from it, which do not permit any short-term measurements. This means that the limits of detection, which can be achieved with these systems, are not sufficient for the analysis of environmental trace quantities.

2. Description of the Related Art

In the EP 0 714 020 A3 a device for the sample-taking of volatile materials including a diffusion body and a means for the adsorption of volatile materials to be collected is described. Here a radially-symmetrical arrangement of a central collector phase, which is placed concentrically within a cylindrical diffusion body, is disclosed. The diffusion path has been substantially shortened with respect to conventional devices, which, it is true, results in a better ratio of surface to diffusion path, but the diffusion path still amounts to more than one millimeter and contains no provisions for the increase of the selectivity of the analytes to be collected. In particular, in the case of this device the moisture, which will have a strong adverse effect during the subsequent analysis, gets unhindered into the collector phase. Furthermore, a design involving a central collector cartridge and open side surfaces (steel wire grid) is complicated and makes it harder to use fine-pored or liquid collector phases, which will then fall out through the metal grid. For reasons of stability, the large surface regions of the collecting phase are, in this case, covered by the metal and reduce the effective diffusion surface. Moreover, this device must be taken apart during the subsequent thermal desorption, in order to heat the collector phase rapidly and effectively by close contact with heated surfaces. During this process the interfering components can enter and distort the result. Due to the air gap between the cylindrically shaped outer plastic body and the centrally symmetrical collecting tubes, this device cannot be used for the passive taking of samples in the case of liquid samples. If one needs to conduct a solvent eluation due to heavy volatile analytes, then, in this case it is necessary, because of the tube-shaped adsorption cartridge with an open perimeter, to use once more an exactly fitting eluation container, which prevents that the solvent escapes through the metal weave. But this results in the formation of small cracks and gaps, which, because they generate a so-called dead volume, delay the washing away of the collected analytes and achieve the desired quantitative transfer to an analysis system only with a high degree of dilution.

From the DE 37 35 307 a diffusion collector is known, which contains a collector phase which is in contact with the phase containing the analytes to be detected by way of a channel-shaped settling path, which is bounded by walls. In this case, the housing can be equipped with perforations, which permit the introduction of water vapor for expelling the substance, the concentration of which was increased in the collector phase.

From WO 96/07885 A1 a collector for chemical analyses is known, in which the receiving part for analytes is covered with a membrane, and where at opposite ends of the receiving part an inlet and an outlet are present. In the case of this collector, however, it only involves a filter, with which a membrane-specific separation can be carried out and where the separated materials can be passed on to a device with which a chemical analysis can be conducted.

By J. A. Johnson and L. Mathiasson in "Supported liquid membrane techniques for sample preparation and enrichment in environmental and biological analysis", Trends in Analytical Chemistry; 11 (1992) March; No. 3, Amsterdam pp. 106–114 possibilities for the collection, preparation and enrichment of analytes are described. In this context a liquid membrane as well as a donor-acceptor complex are used in order to achieve a targeted separation by means of the membrane, which is at least supported by the specific donor-acceptor complex. Furthermore, the transport of material through the membrane is supported by pumps, so that in this case it only involves extremely limited and passively implemented processes, which cannot be used indiscriminately at just any location under the most varied conditions. Thus, for example, neutral material components can only reach equal concentrations on both sides of the membrane.

Starting with the disadvantages of the state of the art, the invention is based on the task of creating a diffusion collector and a process for taking samples in a passive way by means of a diffusion collector which are not very susceptible to being contaminated, can also be used in liquids and permit a quantitative evaluation of the collected sample. The device should have a compact construction and be usable in a versatile manner.

This objective is being achieved by a diffusion collector for gaseous analytes contained in fluid phases comprising a housing which includes at least one indentation in the form of a channel, the at least one channel being provided with an inlet pipe and an outlet pipe and a hydrophobic diffusion membrane permeable for the analyte and covering the at least one indentation, wherein a collector phase is stored in the at least one indentation. This objective is also achieved by a process for the passive taking of samples by means of a diffusion collector wherein the gaseous analyte is diffused through a hydrophobic membrane, which is permeable for the analyte, from the fluid phase into a collector phase, during which process the collector phase is interspersed with a fluid medium for the discharge of a substance to be detected, and where the discharge of the substance to be detected occurs perpendicularly to the direction of diffusion. Each of the sub-claims relates to preferred and advantageous embodiments of the invention.

The diffusion collector according to the invention for gas-type analytes contained in fluid phases includes a planar housing with at least one channel-type indentation, in which a collector phase is retained. The collector phase is covered by a diffusion membrane which is permeable for the analyte.

Besides the diffusion membrane, which is optimized with respect to the analyte and/or the collector phase, the planar construction and the fact that the collector phase has been applied in a thin layer, are essential for this device, and especially the fact that after a sample has been taken, the collected and more highly concentrated analytes are removed from the channel-like indentation, which is oriented almost perpendicularly with respect to the direction of diffusion and by means of which a gaseous or liquid transport current flows through the entire collector phase, which is configured in the shape of a channel. The collector channel according to the invention corresponds with respect to its flow characteristics to a chromatographic column, which was cut open. By virtue of the complete closure of the receiving phase proper, the device can be operated in an extremely simple fashion. For the elution of the collected analytes with a liquid it is not necessary to disassemble anything, because the housing is equipped with at least one inlet pipe and one outlet pipe, which are connected to the collector channel.

For the transport of the collected analytes by means of a carrier gas and an increase of the temperature (thermodesorption) into the analysis apparatus in question, it is likewise not necessary to disassemble the device according to the invention. Here, by means of an enclosed structure, one makes sure that no foreign materials can enter during this process. By means of a suitable and tight covering of the absorption surface and the connecting nipple, the device can be stored or transported without any distortion. The covering of the absorption surface remains in place during the desorption or while it is flushed out with a solvent.

By doing this, an effective transfer of the analyte, for example by means of thermal desorption, is possible. This relinquishment of any disassembly and thus the protection against any further contact with the environment is a must for reliable trace analyses.

According to the invention, an advantageously larger diffusion cross-section, a smaller diffusion path and a more efficient analyte transfer into an analysis device can be achieved by several measures, which alone or together guarantee the goal of a more universal applicability. In this manner an improvement of the analytical collection limits and a drastic increase in the sample-taking frequencies (increase of the temporal resolution capability) are possible. As the driving force for the transport of the analytes through the membrane, osmosis can be used.

In the case of a planar, laminate-like structure of the diffusion collector, a thin, transport-hindering and semipermeable membrane is spread directly above the adsorbent (receiver phase), as a result of which the diffusion path almost reaches zero. With a simultaneously present large diffusion cross-section, such very high collection rates are possible, while at the same time any interfering components are separated by means of diffusion membranes, which are tailor-made for the analytes. Thus, for example, the damaging effects of moisture can be circumvented by the use of hydrophobic, gas-permeable membranes with thicknesses of less than 1 mm and pore widths of between 0.01 and 100 $\mu m$, which are made from PTFE (Teflon®, pore size>10 $\mu m$), Goretex or another water-repelling material (for example silicon rubber, siloxane etc.). In this way, even gases which are dissolved in liquids, can likewise be collected passively. Conversely, it is possible, for example, to preferably transport analytes of greater polarity through hydrophilic membrane materials and thus to collect them.

For use as a hydrophilic membrane or one that is permeable for the solvent in question with typical thicknesses from 10–1000 $\mu m$ and pore sizes of from 10–1000$\mu m$ (e.g. dialysis membranes), such chemically resistant materials as cellulose ester, PVC, polyurethane or other plastics with diffusion channels in the micrometer range or frits, whose surface was chemically modified, should be considered. For the collection of heavy volatile analytes from liquids, membranes with fluid-like transport abilities are used according to the invention. Besides the Langmuir-Blodgett layers (lipid bilayers) with analyte-permeable biochemical analyte channels, membrane-supported liquid membranes as well as thin semipermeable plastic membranes, such as those used for ultrafiltration or dialysis, are also suitable for this purpose. According to the invention the selectivity of these diffusion membranes, which in the passive sample-taking process have initially only the task of compensating for different types of convection during the sample-taking process, can be increased in that, in the case of analyte molecules, the pore width of the membrane and the polarity are adapted to the analytes to be collected, which does not present a problem to an expert. In the case of analyte ions, a more or less selective carrier (ionophore) within the membrane phase together with a charge equalization will be required for the transport through this diffusion membrane. In this process, either the ionophore itself or an additional counterion, which is linked to the membrane phase, can take care of the ion equalization, so that the analyte ion can be transported through the thin membrane phase in the form of a pair of ions. Complex-generating substances and guest molecules are also suitable for serving as membrane-transport partners. According to the invention, all that is known with regard to the active and passive membrane transport, can be applied to this new sample-taking device.

The collector phases are used preferably with thicknesses between 0.01 and 10 mm, in which case the surface facing the membrane may be maximized. The collector phases can thus also be covered on more than one side by a membrane.

A further step according to the invention contributes additionally to the avoidance of problems and prevents an overload of the receiver or collector phase by contaminating components, in particular when a large surplus of the latter is present. For this reason, the analytes to be determined must be bound in the region behind the diffusion membrane more or less selectively by one of the reaction partners, which remain stationary at this location, so that a concentration gradient above the membrane is formed only for the materials to be collected, which leads to an analyte-specific diffusion rate, which depends on the analyte concentration in the adjacent sample space (dispenser phase).

In the receiving or collecting phase, therefore, it is necessary, by means of selective chemical, biochemical or physical-chemical measures, to see to it that at least during the taking of samples the concentration of free analytes is kept at a level, which is lower by orders of magnitude (>>10) than it is in the dispenser phase. This reduction of the concentration of free analytes in a solid, glass-like, liquid, powder- or gel-like collecting phase, of the types that are known, for example, from gas chromatography as stationary phases, can occur in a reversible or a non-reversible manner. In the former case the analytes are released again by physical or physical-chemical effects (e.g. thermodesorption) after the sample was taken, in the second case they are removed from the collector phase together with the selective reagent as a new type of compound, preferably by means of a suitable solvent for the analysis. Examples of collector phases for the first case are: Tenax® TA (polymer of the 2, 6-diphenyl-p-phenyleneoxide), activated charcoal, charcoal made of coconut shells, Carbotrap C (graphitized soot), Carboxen, carbowax phases, organic or inorganic molecular sieves, carrier-bound or free polymer phases having a high boiling point, silica gels, reversed phase stationary chromatographic material, reagent-covered carrier material of a very fine grain size (>>100 µM), for example for aldehyde: silica gel covered with 2, 4 denitrophenehydrazine. For reagents, which selectively bind the analyte in the collector phase, all known detection reagents for the analyte in question are suitable, where, for example, precipitates, complexes or ion pairs are generated.

Versatile collector phases can be produced by the use of immune-chemical reactions. Here it is possible to use correspondingly selective mono- or polyclonal antibodies alone or in a mixture, while liquid as well as gel-like receiving phases are possible. However, besides antibody-antigen reactions other biochemical binding reactions (e.g. DNA-complementary DNA, RNA-complementary RNA, etc.) are also suitable for the purpose of intercepting the analytes.

Furthermore, besides an electrochemical evaluation, a direct indication of the amount of analyte present on the adsorption means is also possible, if the selective reagent, which is binding the analyte, produces a discoloration which is visible to the eye. The latter can then be evaluated semi-quantitatively by means of comparative color charts. The analyte-specific coloration can be measured inside or outside the device. In the case of a measurement where the analyte remains inside the device, the base structure is made of a transparent material (glass, plastic).

BRIEF DESCRIPTION OF THE DRAWINGS

Preferred embodiments and further modifications of the inventions can be seen in the examples of the embodiments and the figures. The following is shown.

DESCRIPTION OF THE PREFERRED EMBODIMENTS

Figure 1:
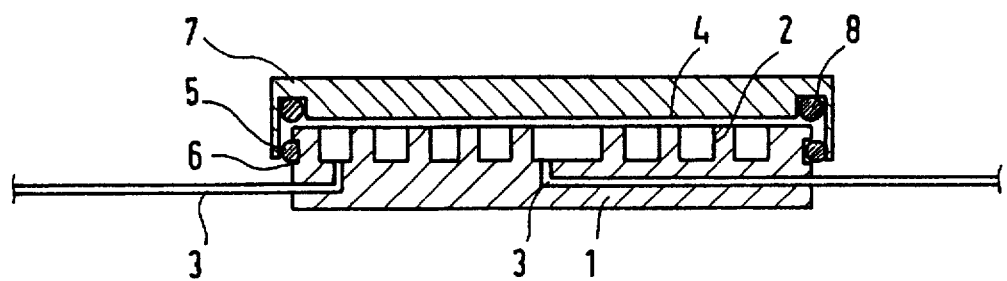
FIG. 1: A cross-section through a diffusion collector according to the invention
Figure 2:
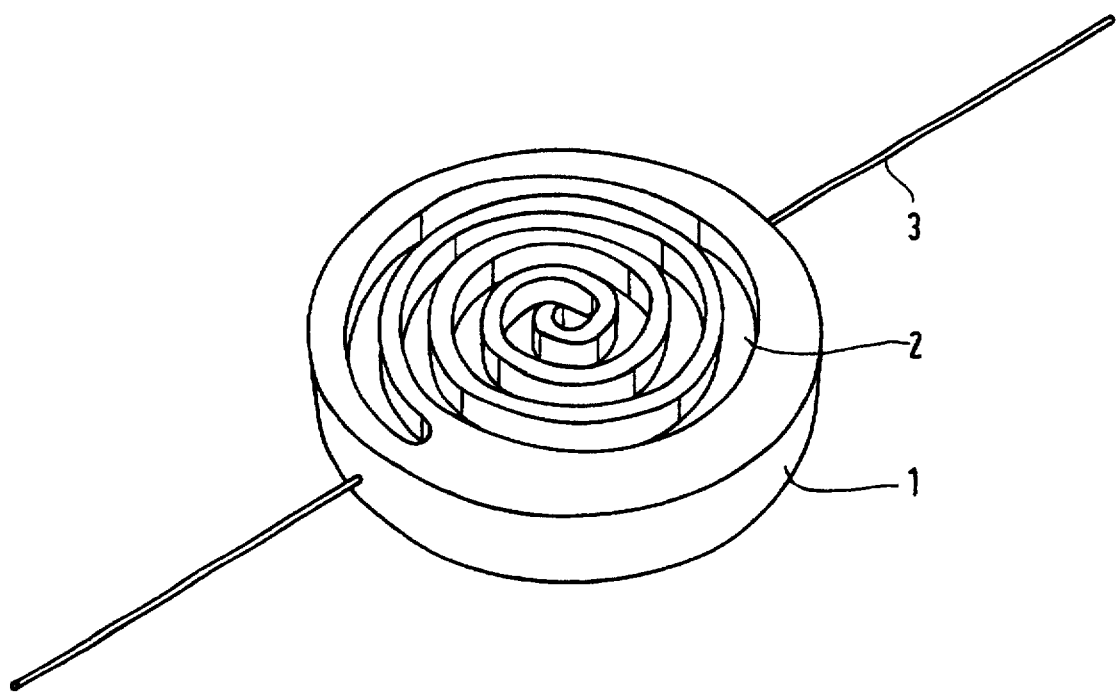
FIG. 2: A top view of the diffusion collector according to FIG. 1.

One of the many possible embodiments of the device according to the invention according to the FIGS. 1 and 2 is designed in such a way that the sample-taking device has the configuration of a portable badge and consists, for example, of a flat disk 1 made of brass of a diameter of about 40 mm and a thickness of about 8 mm, into which a spiral-shaped groove has been machined, which functions as the eluation channel 2 of a depth and width in the micrometer or millimeter range. This channel is, as FIG. 2 shows, accessible at both ends from the outside through the pipe lines 3, which have the configuration of stainless steel capillaries. The diffusion membranes 4 are held in place with a retaining o-ring 5 and a corresponding indentation 6 in the base structure 1. An additional transport cover 7 can seal the sample-taking device for storage or transport purposes by means of a further sealing ring 8.

In the case of a construction method involving brass or Teflon®, PTFE, a material which is based on silicon or siloxane, or where the material for the membrane involves an analogous nucleopore material, thermo-desorption temperatures >200° C. can be used. The materials should be temperature resistant up to at least 400° C. The exact form of the eluation channels and the material of the base body (spiral-shaped or meander-shaped) is unimportant and depends on the particular type of application. If a thermo-desorption is carried out, it is preferable to use non-corroding metals or alloys for this. In the case of a solvent extraction, chemically resistant plastics are used for this purpose.

With a groove length of about 200 mm and a width of about 2.5 mm a diffusion cross-section of about 5 $cm_2$ results. Into this groove the receiver phase being used (an adsorption means or some other collector phase) is inserted up to its upper edge. Over this disk, the semipermeable diffusion membrane or a number of them (thickness in the micrometer range), which is optimized for the analyte, is stretched, and it can be held in place with the help of an o-ring. In such an arrangement the collector phase extends up to the membrane, so that the diffusion path, which characterizes every passive collector, is almost equal to zero.

As an alternative, the diffusion body can also be generated on-site, i.e. one or several membranes, which have been optimized with respect to the analytes (preferred transport), can be placed on the planar surface of the device by means of spraying or by the so-called spin coating process with subsequent polymerization (photochemically or otherwise). Stable Langmuir-Blodgett-films are then obtained by means of dipping the device, which is filled with the collector phase, into a Langmuir-balance trough, with a subsequent stabilizing polymerization (e.g. photo-polymerization or chemical polymerization).

Inlet and outlet pipes for the gaseous or liquid transport current can still be attached to the device, which pipes always start at the two ends of the groove. The other end of these inlet and outlet pipes can, for example, be attached to the rear surface or the lateral surfaces. There the connection for supplying it with the transport medium and for its removal to an analysis device is made. By means of such an arrangement it is possible, according to the invention, to guide a transport flow perpendicularly with respect to the direction of diffusion through the entire adsorption means, whereby a quick and quantitative desorption of the analytes without peak tailing through dead angles is made possible. After a sample has been taken, the device can be installed directly, without any further preparation, in an appropriate thermo-desorption apparatus or liquid eluation apparatus.

When TENAX TA was used as an adsorption means and a micro-porous PTFE membrane (pore width 10 µm) was used during a sample-taking time of 8 h, such a device made it possible to achieve mean receiving rates of 30 to 45 cm³/min.

It has proved to be advantageous during the transport of the device and during its storage to attach a tightly closing lid at the side, to which the membrane is attached, because in this manner the further reception of analytes outside the sample-taking time proper is avoided. This can also be achieved by the storage of the device during this time in an airtight closed container.

The absolute size of the device is unimportant. It is also possible to produce versions on the millimeter scale with the modern production methods of the micro system technology, above all when the diffusion membranes are made by spin coating on a wafer with many devices at the same time.

EXAMPLES

1. Sample-taking of BETX

For the determination of benzene, ethyl benzene, toluene, p-xylene, m-xylene and o-xylene in extremely low concentrations in an interior space, about 250 mg of Tenax TA, which was packed firmly into the channels of the device, was used as the receiver phase. This resulted in a cross-section for the diffusion boundary surface of 5.25 cm². A PTFE membrane with a mean pore width of 10 μm was used as a diffusion body. The diffusion thickness was about <<1 mm. For releasing the analytes the technique of thermo-desorption was applied. As an analysis device a gas chromatograph with AED was used.

A device according to the invention, which has the configuration of a badge that can be pinned on, makes it possible, for example, to collect samples at a rate of about 1 l/h for benzene, 2.5 l/h for ethyl benzene, 2 l/h for toluene, 2.5 l/h for p-xylene, 2.3 l/h for m-xylene and 1.6 l/h for o-xylene. The limits of detectability, that are achievable, lie in the pg-range. Compared to the state of the art, the passive sample collector according to the invention reduces the collecting phase to about ¹/₁₀. This constitutes a great advantage, because now even smaller temporal fluctuations of the analyte can be detected.

In this case, the device according to the invention reduces the collecting time as compared to the state of the art to about <20%.

2. Sample-taking and Measurement of Ozone in Air.

For this purpose a base structure of the configuration and dimensions mentioned above located inside a transparent plastic (e.g. plexiglass®) was used. As a diffusion body a stretched Teflon® membrane of a thickness of <50 μm and a mean pore diameter of <10 μm was used. As a receiver phase an aqueous gel (Agar-Agar) with about 5% potassium iodide and <5% starch (e.g. potato starch) and with an addition of 5% magnesium nitrate was used. After a predetermined collection time the blue-black discoloration of the collector phase is "converted" into an ozone concentration by comparing it with color charts. Thus, ppb-quantities can be easily determined within a few hours.

2. Sample-taking of Lead in Aqueous Samples

For the determination of very low lead concentrations a passive collector was assembled, which contained as the receiver phase a gel of polyvinyl alcohol (PVA), saturated with dithizone. As a membrane a very thin PVC foil (30% PVC, 60% diphenyl ether) and 10% of a lead ionophore (used for ion-selective membranes) was used. The device makes it possible as in the 2nd example to estimate the lead content merely by the coloration of the dithizone-containing phase.

3. Sample-taking of herbicides on the Basis of the Example of 2, 4 Dinitrophenoxy Acidic Acid In this case a receiver with antibodies for this analyte was applied behind a foil-type dialysis membrane with a molecular cut-up of 10,000 dalton. The analyte-antibody bond was split by means of a urea solution acting as a chaotropic reagent and the analyte was determined in the traditional manner.

4. Sample-taking and measurement of glucose

Here a dialysis membrane is used as a diffusion membrane, and the receiver phase corresponds to the ozone measurement in air, with the only distinction, that here the enzyme glucose oxidase is also present.

What is claimed is:

1. A diffusion collector for gaseous analytes contained in fluid phases, comprising:
   a housing with at least one indentation in the form of a channel, said at least one indentation being provided with an inlet pipe and an outlet pipe; and
   a hydrophobic diffusion membrane permeable for the analyte and covering the at least one indentation;
   wherein a collector phase is stored in the at least one indentation.

2. A diffusion collector according to claim 1, wherein the inlet pipe and outlet pipe are always placed at opposite ends of the at least one indentation.

3. A diffusion collector according to claim 1, wherein the inlet pipe and the outlet pipe are fashioned as capillaries.

4. A diffusion collector according to claim 1, comprising a diffusion path between the two phases, wherein the collector phase and the phase containing the analyte are separated by the membrane and are adjacent each other and that the diffusion path between the two phases amounts to less than 1 mm.

5. A diffusion collector according to claim 1, wherein the at least one indentation is made in the shape of a spiral.

6. A diffusion collector according to claim 1, wherein the housing and membrane are made of a temperature-resistant material.

7. A diffusion collector according to claim 1, wherein the diffusion collector also includes a tightly fitting cover for the collector phase.

8. A diffusion collector according to claim 1, wherein the collector phase contains at least one phase, which selectively binds the analyte.

9. A diffusion collector according to claim 1, wherein the collector phase contains at least one phase, which selectively transplants the analyte.

10. A diffusion collector according to claim 1, wherein the collector phase has a maximized surface on a side which faces the membrane.

11. A diffusion collector according to claim 1, wherein the collector phase is covered by the membrane on two or more sides.

12. A diffusion collector according to claim 1, wherein the membrane is a semipermeable diffusion membrane.

13. A diffusion collector according to claim 1, wherein the membrane is attached to the housing by means of an o-ring.

14. A diffusion collector according to claim 1, wherein the membrane is put in place by means of an on-site coating process.

15. A diffusion collector according to claim 1, wherein a fluid medium, which is conveyed through the at least one indentation is a carrier gas or a carrier solution.

16. A diffusion collector according to claim 1, wherein the diffusion collector is made in the form of a badge.

17. A diffusion collector according to claim 1, wherein the collector phase contains at least an ad- or absorption means suitable the analyte.

18. Process for the passive taking of samples with a diffusion collector according to claim 1, wherein the gaseous analyte is diffused through a hydrophobic membrane, which is permeable for the analyte, from the fluid phase into a collector phase, during which process the collector phase is interspersed with a fluid medium for the discharge of a substance to be detected, and where the discharge of the substance to be detected occurs perpendicularly to the direction of diffusion.

19. Process according to claim 18, wherein as the substance to be detected, the analyte itself or the analyte in a chemically or biochemically converted form, is discharged.

20. Process according to claim 18, wherein for the purpose of discharging the substance to be detected, a release of the substance to be detected by means of chemical solvation or thermal desorption is carried out.

21. Process according to claim 18, wherein the analyte is transported through the membrane by means of active transport mechanisms.

22. Process according to claim 18, wherein the analyte is transported through the membrane (4) by means of passive transport mechanisms.

23. Process according to claim 18, wherein the analyte is transported through the membrane by means of osmosis.

24. Process according to claim 18, wherein the collector phase is evaluated colormetrically after the sample is taken.

\* \* \* \* \*